United States Patent
Lang

(12) 
(10) Patent No.: US 6,194,420 B1
(45) Date of Patent: Feb. 27, 2001

(54) 2-AMINO-5,6-DICHLORO-3,4-DIHYDROQUINAZOLINE, ITS METHOD OF MAKING AND USING AND PHARMACEUTICAL COMPOSITIONS THEREOF

(75) Inventor: Philip C. Lang, Toms River, NJ (US)

(73) Assignee: Roberts Laboratories Inc., Eatontown, NJ (US)

( * ) Notice: Subject to any disclaimer, the term of this patent is extended or adjusted under 35 U.S.C. 154(b) by 0 days.

(21) Appl. No.: 09/452,008

(22) Filed: Nov. 30, 1999

(51) Int. Cl.$^7$ .................. C07D 487/04; A61K 31/625
(52) U.S. Cl. .................. 514/259; 514/260; 544/283
(58) Field of Search .................. 544/283, 286; 514/259

(56) References Cited

U.S. PATENT DOCUMENTS

| | | |
|---|---|---|
| Re. 31,617 | 6/1984 | Beverung, Jr. et al. . |
| 2,862,966 | 12/1958 | Surrey . |
| 3,932,407 | 1/1976 | Beverung, Jr. et al. . |
| 4,146,718 | 3/1979 | Jenks et al. . |
| 4,208,521 | 6/1980 | Crenshaw et al. . |
| 4,357,330 | 11/1982 | Fleming, Jr. et al. . |
| 5,801,245 | * 9/1998 | Lang .................. 544/250 |

OTHER PUBLICATIONS

Stalder., Helv. Chim. Acta., vol. 69, 1986 pp. 1887–1897.*
Disposition of anagrelide, an inhibitor of platelet aggregation; Clinical Pharmacology and Therapeutics; Gaver et al.; vol. 29; 1981; pp. 381–386.
Focus on Anagrelide; Drugs, May 1994; vol. 5; pp. 809–822; Issn: 0012–6667.
Analysis of the Mechanism of Anagrelide–Induced Thrombocytopenia in Humans; Eric M. Mazur et al.; Blood; vol. 79; No. 8; Apr. 15, 1992; pp. 1931–1937.
Agrylin (anagrelide hydrochloride); Product Monograph; Roberts Pharmaceuticals Corp.; 1997.
Anagrelide for Control of Thrombocythemia in Polycythemia and Other Myeloproliferative Disorders; Petitt et al.; Seminars in Hematology; vol. 34; No. 1, (Jan.); 1997; pp. 51–54.
Anagrelide, a selective thrombocytopenic agent, American Journal of Health–System Pharmacy, vol. 55, Oct. 1, 1998; pp. 1979–1986.
Blood; Journal of the American Society of Hematology; W. R. Saunders Company; vol. 94; No. 10; Supplement 1 (Part 1 of 2); Nov. 15, 1999; p. 701a.

* cited by examiner

*Primary Examiner*—Mukund J. Shah
*Assistant Examiner*—Pavanaram K Sripada
(74) *Attorney, Agent, or Firm*—DeLio & Peterson LLC

(57) ABSTRACT

The compound 2-amino-5,6-dichloro-3,4-dihydroquinazoline has been found to have enhanced platelet count reducing properties. Also provided are methods for synthetically making the compound and a method of reducing the platelet count in a patient by administering to the patient a platelet reducing effective amount of the compound preferably together with a pharmaceutically acceptable carrier. A pharmaceutical composition is also provided which contains the above compound as the active ingredient together with pharmaceutically acceptable excipients.

15 Claims, No Drawings

2-AMINO-5,6-DICHLORO-3,4-DIHYDROQUINAZOLINE, ITS METHOD OF MAKING AND USING AND PHARMACEUTICAL COMPOSITIONS THEREOF

BACKGROUND OF THE INVENTION

1. Field of the Invention

This invention relates to the treatment of thrombocythemia, secondary to myeloproliferative diseases, such as Essential Thrombocythemia (ET), Polycythemia Vera (PV), Chronic Myelogenous Leukemia (CML), and Other Myeloproliferative Diseases (OMPD) using an effective amount of the preferred active compound 2-amino-5,6-dichloro-3,4-dihydroquinazoline.

2. Description of Related Art

Anagrelide, which is chemically 6,7-dichloro-1,5-dihydroimidazo-[2,1-b]-quinazolin-2(3H)-one, is indicated for the treatment of patients with thrombocythemia, secondary to myeloproliferative diseases, such as Essential Thrombocythemia (ET), Polycythemia Vera (PV), Chronic Myelogenous Leukemia (CML), and Other Myeloproliferative Diseases (OMPD).

The formula for Anagrelide is:

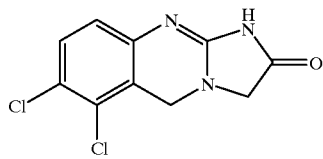

(A)

The major clinical action of Anagrelide is to decrease and maintain the platelet count within normal limits. The most common adverse effects associated with the use of Anagrelide are related to its vasodilatory and positive inotropic effects. Cardiovascular side effects associated with the use of Anagrelide have included: vasodilation (<5%), tachycardia (7.5%), palpitations (26.1%), and congestive heart failure (1.5%).

A study by Gaver et al. (1981) "Clinical Pharmacology and Therapeutics", 29, 381–392, demonstrated that Anagrelide was extensively metabolized by human subjects to a minimum of at least four to five compounds excreted in the urine and that peak plasma concentrations of the parent drug were only 6 ng/mL. It was reported that very little of the Anagrelide dose (<1%) was excreted as unchanged drug in the urine. These studies raised the possibility that the thromobocytopenia observed with Anagrelide may be due to a metabolite rather than the parent drug. In the Gaver study the use of $^{14}$C-anagrelide indicated by HPLC a minimum of four to five metabolites which accounted for over 75% of the urinary radioactivity. It was concluded that the antiaggregation activity observed in humans is possibly related to the presence of Anagrelide and an active metabolite(s).

U.S. Pat. No. 3,932,407 and its Reissue Pat. No. Re. 31,617, which patents are hereby incorporated by reference, disclose Anagrelide type compounds of the formula:

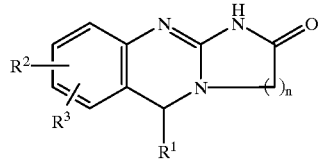

(B)

in which $R^1$ is H, phenyl or lower alkyl, $R^2$ and $R^3$ when alike are H, chloro, bromo, fluoro, lower alkyl, hydroxy or lower alkoxy, $R^2$ and $R^3$ when different are H, chloro, bromo, fluoro, $SO_3H$, $CF_3$, hydroxy, nitro, amino, phenyl, lower alkyl of 1 to 3 carbon atoms or lower alkoxy of 1 to 3 carbon atoms, or when taken together $R^2$ and $R^3$ are methylenedioxy or the residue of phenyl ring, and n is an integer of 1 or 2; and pharmaceutically acceptable acid addition salts thereof. The compounds, which are disclosed as hypotensive, blood platelet reducer and/or bronchodilator agents, are prepared inter alia by a multistep process ending in the reaction of CNBr with an ethanol solution of a compound of the formula:

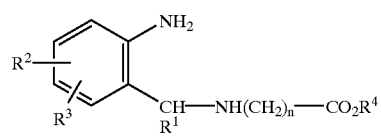

(C)

in which $R^1$, $R^2$, $R^3$ and n are as described above, and $R^4$ is lower alkyl.

Anagrelide having the chemical name 6,7-dichloro-1,5-dihydroimidazo[2.1-b]quinazolin-2[3H]-one and the structural formula shown as (A) above is of particular interest because it is known to be a potent reducer of platelet count induced by a variety of aggregating agents.

Anagrelide may be prepared directly from a lower alkyl-N-(6-amino-2,3-dichlorobenzyl)glycine of Formula (C) by reaction in an alcoholic solution with CNBr. U.S. Pat. No. 4,146,718 incorporated herein by reference, discloses an improved process whereby higher yields of Anagrelide may be obtained by reacting a compound of Formula (C) with, for example, CNBr, CNCl or CNI in an inert, aprotic organic solvent and isolating the novel intermediate of Formula D.

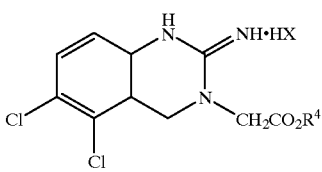

(D)

wherein $R^4$ is (lower)alkyl and X is chloro, bromo or iodo. In a preferred embodiment X is bromo and $R^4$ is methyl, ethyl, n-propyl, isopropyl or n-butyl. In a more preferred embodiment X is bromo and $R^4$ is methyl, ethyl or n-propyl. In a most preferred embodiment X is bromo and $R^4$ is ethyl.

Intermediate Compound (D) is then treated with a base to produce the Anagrelide compound of Formula A.

As reported in U.S. Pat. No. 4,146,718, supra, although the compounds of Formula (D) are primarily intended as intermediates in the preparation of Anagrelide, they themselves have blood platelet antiaggregative properties.

Bearing in mind the problems and deficiencies of the prior art, it is therefore an object of the present invention to provide a compound which has enhanced platelet reducing properties without side effects of presently used compounds such as Anagrelide.

It is another object of the present invention to provide a method for making a compound having enhanced platelet reducing properties.

A further object of the invention is to provide a method for reducing the platelet count in a patient by administering a platelet reducing amount of a compound having enhanced platelet reducing properties preferably with a pharmaceutical carrier in a unit dose.

It is yet another object of the present invention to provide a pharmaceutical composition containing a compound effective for reducing the platelet count together with pharmaceutically acceptable excipients.

Still other objects and advantages of the invention will in part be obvious and will in part be apparent from the specification.

SUMMARY OF THE INVENTION

It has now been discovered that a compound of the following formula has enhanced platelet reducing properties:

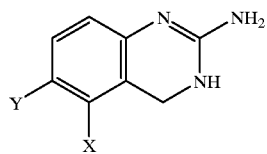
(E)

wherein at least one of X or Y is Cl, Br or F and the other is Cl, Br, F, OH, $OCH_3$, $NHCOCH_3$ or $CONH_2$; and pharmaceutically acceptable addition salts thereof; and tautomers thereof as shown below as (F).

In a preferred embodiment Y and X are both Cl and the compound is 2-amino-5,6-dichloro-3,4-dihydroquinazoline.

In another aspect of the invention a method for making compound (E) comprises the steps of:

(a) nitrating a compound of the formula (G):

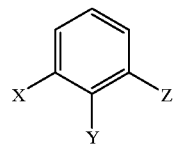
(G)

to form a compound of the formula (H):

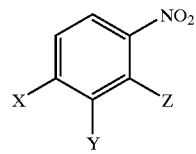
(H)

wherein X, Y and Z are independently Cl, Br or F;

(b) reacting compound (H) under cyanation conditions to form a compound of the formula (I):

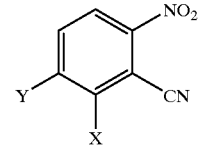
(I)

(c) reacting compound (I) under reducing conditions to form a compound of the formula (J):

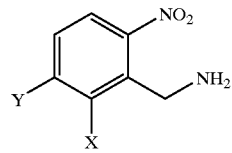
(J)

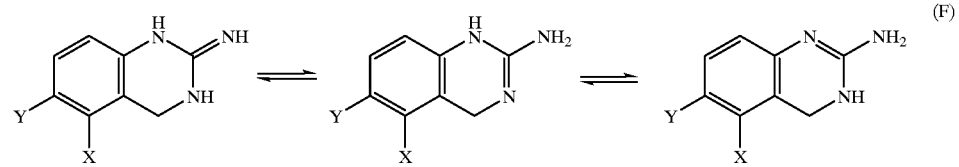
(F)

(d) reacting compound (J) under reducing conditions to form a compound of the formula (K):

(K)

(e) reacting compound (K) with CNZ to form the desired compound (E) as an HZ salt:

(E)

·HBr wherein Z is Cl, Br or F.

In a further aspect of the invention a process is provided for making compound (E) starting from 2,3-dihalobenzaldehyde comprising the steps of:
(a) nitrating a compound of the formula (L):

(L)

to form a compound of the formula (M):

(M)

wherein X and Y are independently Cl, Br or F;
(b) hydroxylating and halogenating compound (M) preferably in in situ sequential reactions to form a compound of the formula (O) with intermediate (N):

(N)

(O)

wherein Z is Cl, Br or F;

(c) aminating compound (O) to form a compound of the formula (P):

(P)

(d) reducing compound (P) to form a compound of the formula (Q):

(Q)

(e) cyanating compound (Q) to form the desired compound (E) as a HBr salt:

(E)

·HBr

In a further aspect of the invention, compound (M) is reductively aminated to form compound (P) and the process continued in step (d) as shown above to make the desired compound (E).

In a further aspect of the invention a method is provided for reducing the platelet count in a patient which comprises administering to the patient a platelet reducing effective amount of a compound of the formula of compound (E), preferably in combination with a pharmaceutical carrier. The compound is administered in a unit dosage form typically in the form of a capsule, tablet, enteric coated tablet, IV formulation or nasal spray.

In another aspect of the invention a pharmaceutical composition is provided containing as the active ingredient at least one compound as in formula (E) together with pharmaceutical acceptable excipients such as mannitol and methyl cellulose. The pharmaceutical composition is in a unit dosage form which is administered to patients taking the pharmaceutical composition.

DESCRIPTION OF THE PREFERRED EMBODIMENT(s)

Compounds of the formula E have been found to have enhanced platelet reducing properties:

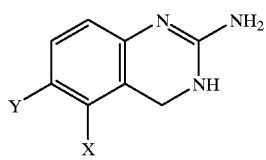

wherein at least one of X or Y is Cl, Br or F and the other is Cl, Br, F, OH, OCH₃, NHCOCH₃ or CONH₂; and pharmaceutically acceptable addition salts thereof; and tautomers thereof.

2-amino-5,6-dichloro-3,4-dihydroquinazoline is the preferred compound for use in reducing the platelet count in patients and is preferably provided as the hydrobromide salt which is water soluble. This is to be compared with Anagrelide hydrochloride which is nearly insoluble in water.

Compound E has been synthesized and has been found to be an active molecule for causing reduction of platelet counts, without the side effects of inotropy and hemorrhaging associated with Anagrelide. Only very mild antihypertensive activity was noticed during cardiovascular screening of the compound.

As shown below in the Examples, a preferred process is set forth for making 2-amino-5,6-dichloro-3,4-dihydroquinazoline from commercially available starting materials. In one process 1,2,3-trichlorobenzene is used as the starting material and is nitrated using, for example, nitric/sulfuric acids to form 1,2,3-trichloro-4-nitrobenzene. This compound is then reacted with a cyanating agent such as CuCN to form 2,3-dichloro-6-nitrobenzonitrile. The nitrile is then reacted under reducing conditions using for example $B_2H_6$ to form 2,3-dichloro-6-nitrobenzylamine HCl which is then reduced and reacted with CNX to form the desired compound.

In another process, 2,3-dichlorobenzaldehyde is reacted to form 2,3-dichloro-6-nitrobenzaldehyde. The aldehyde is then reacted to form the alcohol and in situ reacted to form the corresponding halomethyl compound. The halomethyl compound is then reacted to form the benzylamine. The benzylamine is reduced to form the diamine and the diamine reacted with CNX to form the desired compound. In another process the 2,3-dichloro-6-nitrobenzaldehyde (above) is reductively aminated to the benzylamine and the process continued to form compound (E).

EXAMPLES

A metabolite of Anagrelide was isolated from human urine and purified by reversed-phase HPLC. Structural characterization was carried out by the use of mass spectrometry and ¹H-NMR spectroscopy. Positive liquid secondary ion mass spectrometry provided an exact mass of the protonated molecule as 216.0080 and a calculated chemical composition of $C_8H_7N_3Cl_2$. The ¹H-NMR spectrum indicated that the compound contained two ortho coupled aromatic protons and two benzylic protons located on a quinazoline ring. Capillary LC/electrospray mass spectrometry showed that the metabolite was a homogeneous single compound which gave an intense protonated molecular ion at m/z 216 with a chlorine isotope peak at m/z 218. In source fragmentation resulted in the generation of structurally significant fragment ions including the loss of a primary amino group and cleavage of the quinazoline ring. Based on these data the metabolite was identified as 2-amino-5,6-dichloro-3,4-dihydroquinazoline. The structure of the metabolite was confirmed by comparison with a synthesized sample.

Metabolism of Anagrelide was examined in a number of in vitro systems including rat and human liver microsomes, human whole blood, human bone marrow cells and rat intestinal mucosa. Surprisingly, under all of the conditions that were tried, Anagrelide was completely resistant to metabolism. It appears that in vivo metabolism occurs by a route that cannot be readily mimicked in vitro. It is hypothesized that the first step of in vivo metabolism involves hydroxylation of the carbon α to the carbonyl followed by amide hydrolysis and loss of the elements of glyoxylic acid.

In a recent pharmacokinetic and excretion study of [¹⁴C] Anagrelide to Rhesus Monkeys, no human metabolite (2-amino-5,6-dichloro-3,4-dihydroquinazoline) was detected, showing that humans uniquely metabolize Anagrelide.

Preparation of 2-Amino-5,6-Dichloro-3,4-Dihydroquinazoline Hydrobromide from 2,3-Dichlorobenzaldehyde Preparation of 2,3-Dichloro-6-nitrobenzlaldehyde A solution of 40 g of 2,3-dichlorobenzaldehyde in 160 mL of concentrated sulfuric acid (95–98% w/w) is heated to 40° C. and stirred to form a solution, then cooled to 20–25° C. Concentrated nitric acid (69–71% w/w; 24.7 g) is added to this solution over 20 minutes (an ice bath is used to maintain a reaction temperature of 20–30° C.). The reaction mixture is stirred at room temperature for 1 hour, and then added in portions to 600 mL of water. The resulting suspension is stirred for 2 hours and filtered. The filter cake is washed (3×50 mL water). The filter cake is agitated with 200 mL of water for 2 hours and filtered. The filter cake is washed (3×50 mL of water) and dried in vacuo to give a mixture of the title product and the isomer, 2,3-dichloro-5-nitrobenzaldehyde.

The crude product is triturated with hexane for 3 hours and filtered. The filter cake is washed with hexane (2×70 mL). This trituration procedure is repeated with fresh hexane until the 5-nitro isomer is removed. The filter cake is then dried in vacuo to give the purified title product in 44 to 50% yield.

Preparation of 2,3-Dichloro-6-nitrobenzylalcohol

A solution of 40 g of 2,3-dichloro-6-nitrobenzaldehyde in 200 mL of toluene was stirred for five minutes. Then, 7.4 mL of methanol was added and mixing continued until all the solids had dissolved. Separately, a solution of 2.41 g of sodium borohydride in 120 mL of toluene was prepared. The benzaldehyde solution was added by drops to the borohydride solution over 20 minutes to maintain the reaction temperature below 25° C. The reaction mixture was stirred for 24 hours at room temperature under nitrogen. Forty mL of water was added and the mixture stirred for 15 minutes. The aqueous layer was removed and the organic layer washed with water (3×40 mL). The organic layer was azeotropically dried using a Dean-Stark trap, and concentrated to 280 mL. The 2,3-dichloro-6-nitrobenzylalcohol was used without further purification.

Preparation of 1,2-Dichloro-3-chloromethyl-4-nitrobenzene

Under nitrogen, 27.9 mL of triethylamine was added to the concentrated solution of 2,3-dichloro-6-nitrobenzylalcohol prepared in the previous step. To this solution, 14.6 mL of thionyl chloride was added via an addition funnel over 15 minutes. Following addition, the solution is heated to 45–50° C. for 18 hours, then cooled to room temperature under nitrogen. Water and toluene are added to the reaction mixture and the mixture filtered. The filtrate is diluted with water, and the aqueous layer removed. The organic layer is washed with water (4×40 mL), and dried by azeotropic distillation. The solution is concentrated to give 1,2-dichloro-3-chloromethyl-4-nitrobenzene which could be used without further purification.

Preparation of 2,3-Dichloro-6-nitrobenzylamine

Potassium carbonate and 2 equivalents of phthalimide are ground together and heated to reflux with 2 equivalents of 1,2-dichloro-3-chloromethyl- 4-nitrobenzene for three hours. Upon cooling, the substituted benzylphthalimide crystallizes and is filtered in 60–80% yield. 2,3-Dichloro-6-nitrobenzylamine is obtained in a 75–95% yield with acid hydrolysis using hydrochloric acid from the substituted benzylphthalimide.

Preparation of 2-Amino-5,6-dichlorobenzylamine

A solution of 7.131 g of tin (II) chloride dihydrate in 4.7 L of concentrated hydrochloric acid was prepared. Separately, 1.631 g of 2,3-dichloro-6-nitrobenzylamine hydrochloride was dissolved in 9.5 L of concentrated hydrochloric acid. The solution of the amine was added to the tin chloride solution over 1–2 hours to maintain the reaction temperature below 45° C. The mixture was stirred for 2 hours at 40–45° C. in a warm water bath, and cooled in an ice/methanol bath to −5° C. The mixture was filtered, and the isolated solids slurried with 13 L water, 6.5 kg ice, and 6 L methylene chloride. Sodium hydroxide (50% aqueous solution) was added until pH >12, and the organic layer was removed. The aqueous phase was extracted with methylene chloride (2×6 L), and the combined organic layers washed with water (6 L portions) until pH=7–8. The organic layers were dried over magnesium sulfate (500 g) and charcoal (200 g) for 16 hours, and filtered. The filtrate was concentrated to an oil, and crystallized from isopropanol at −20° C. to give 2-amino-5,6-dichlorobenzylamine in 58 to 96% yield.

Preparation of 2-Amino-5,6-Dichloro-3,4-Dihydroquinazoline

A solution of 2.58 kg of 2-amino-5,6-dichlorobenzylamine in 2.7 L of toluene was prepared at 50–60°. A solution of cyanogen bromide (1.558 kg in 8 L toluene) was added over 2–3 hours. Following addition, the reaction mixture was stirred for 1.5 hours at room temperature, then heated to reflux for 1 hour. The mixture was cooled to room temperature for 12 hours, and the mixture filtered. The filter cake was washed with toluene (2×2 L) followed by hexane (2×2 L) and dried to give 2-amino-5,6-dichloro-3,4-dihydroquinazoline hydrobromide in 70% to 90% yield.

Characterization of 2-Amino-5,6-Dichloro-3,4-Dihydroquinazoline

Elemental Status

Analysis calculated for $C_8H_7N_3Cl_2 \cdot HBr$: C, 32.35%; H, 2.72%; N, 14.15%; Br, 26.91%; Cl, 23.88%; Found, C, 32.78%; H, 2.73%; N, 13.91%; Br, 27.17%; Cl, 23.90%.

The above method of preparation may be shown by the following equation sequence:

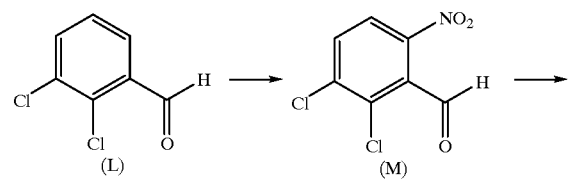

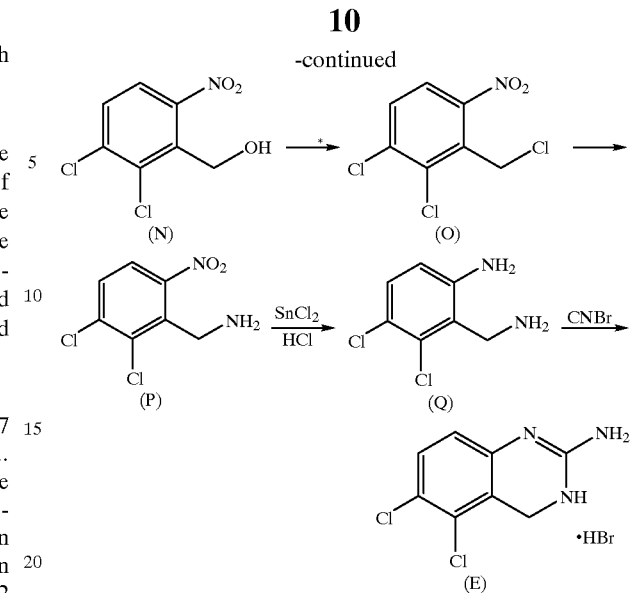

This reaction was run in situ with no isolation of the alcohol from the alcoholization reaction.

In another process of the invention the 2,3-dichloro-6-nitrobenzaldehyde formed above (M) is reductively aminated to form 2,3-dichloro-6-nitrobenzylamine (P) as follows:

A solution of the aldehyde in methanol is stored for 16 hours at room temperature with 10 equivalents of ammonium hydroxide and 0.5 equivalents of sodium cyanoborohydride. The reaction was quenched by the addition of water and 1N HCl. The product amine was isolated by concentration in a 60–84% yield.

Compound (P) is then reacted as above to form the desired compound (E).

Preparation of 2-Amino-5,6-Dichloro-3,4-Dihydroquinazoline Hydrobromide from 1,2,3-Trichlorobenzene Preparation of 1,2,3-trichloro-4-nitrobenzene A mixture of 9.0 kg of 1,2,3-trichlorobenzene in 13.32 L of concentrated sulfuric acid is acid by drops to a solution of 4.13 L of 70% nitric acid and 4.13 L of concentrated sulfuric acid at 25–30° C. The slurry is stirred for 1.5–2 hours, then poured over 35 kg of ice and filtered. The filter cake is washed (15 L water) and then dissolved in 58 L of ethyl acetate. The organic phase is washed with water, aqueous sodium bicarbonate solution, and aqueous sodium chloride solution. The solution is dried over magnesium sulfate and concentrated to give the title product.

Preparation of 2,3-Dichloro-6-nitrobenzonitrile

A solution of 1.831 kg of 1,2,3-trichloro-4-nitrobenzene and 0.861 kg of copper cyanide in 1.21 L of DMF is heated to 155° C. for 2 hours, then cooled to room temperature. A solution of 3.24 kg of ferric chloride hexahydrate, 0.806 L of concentrated hydrochloric acid, and 4.87 L of water is added and the solution heated to 65° C. for 20 minutes. The mixture is cooled, stirred with 0.55 kg of charcoal and 4 L of toluene, and filtered. The organic phase is separated and the aqueous phase extracted with toluene. The combined toluene layers are washed with water and 6 N HCl, dried and concentrated to give a slurry. The slurry is dissolved in 1.5 L of methanol, and stored at 5° C. for 24 hours. The nitrile product is collected by filtration, washed with 1.5 L cold methanol and dried at 40° C.

Preparation of 2,3-Dichloro-6-nitrobenzylamine HCl

A solution of 0.213 kg of 2,3-dichloro-6-nitrobenzonitrile in 1.176 L of dry THF is added to 1.6L of $BH_3$.THF between 0–5° C. The solution is stirred for 2 hours at room temperature, heated to 66° C. for 2 hours, and then cooled to 15° C., before adding 0.329 L of cold methanol. The mixture is held for 17 hours and evaporated under vacuum to an oil. The oil is dissolved in ethyl acetate, cooled to 0° C. and sparged with hydrogen chloride gas. The salt is collected by filtration, washed with cold ethyl acetate, and dried.

As shown above, the nitro group in the above compound is then reduced with $SnCl_2$/HCl to form compound (K) and then reacted with CNBr to make the desired product (E).

The above reaction sequence starting from 1,2,3-trichlorobenzene is as follows:

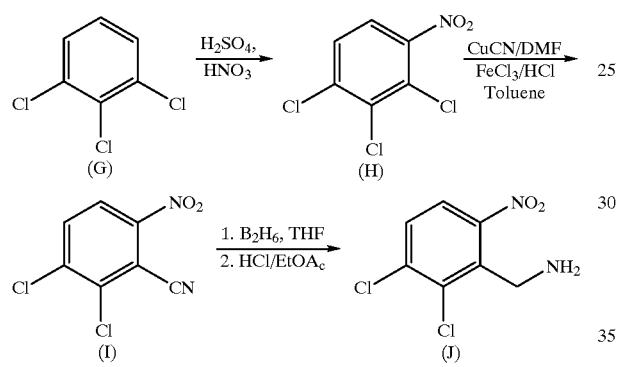

The effectiveness of the compound (E) of the invention is shown wherein daily intraperitoneal injection of the preferred compound in 6 to 8-month old mice resulted in a dose-dependent decrease in circulating platelet levels. Administration of 100 μg/day of the preferred compound was sufficient to decrease platelet counts within 24–48 hours stabilizing to 50% of normal by day 5. Even at high doses (300 μg), the preferred compound did not alter white blood cell counts, bleeding time or lead to any apparent signs of toxicity or hemorrhaging. A profound inhibition of megakaryocytic endoreplication was achieved at doses 500 times less than those reported for Anagrelide. However, there was no effect on the CD15+ myeloid lineage suggesting that even in vitro the preferred compound selectively affects megakaryocytic lineage, but unlike Anagrelide, the compound did not inhibit platelet aggregation even at high concentrations (10 μg/mL).

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A compound having the following formula:

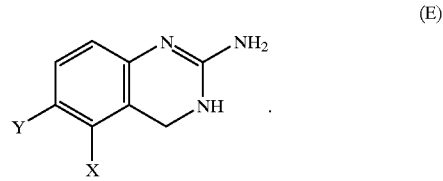

wherein X and Y is Cl, Br or F; and pharmaceutically acceptable addition salts thereof; and tautomers thereof.

2. The compound of claim 1 wherein both X and Y are Cl.

3. The compound of claim 2 in the form of the HBr salt.

4. A method for making a compound of the formula:

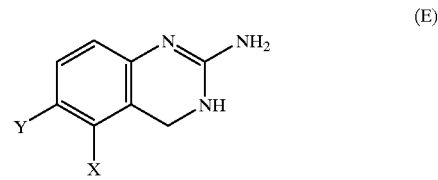

comprising the steps of:

(a) nitrating a compound of the formula (G):

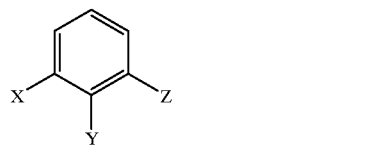

to form a compound of the formula (H):

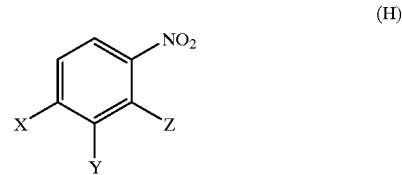

wherein X, Y and Z are independently Cl, Br or F;

(b) reacting compound (H) under cyanation conditions to form a compound of the formula (I):

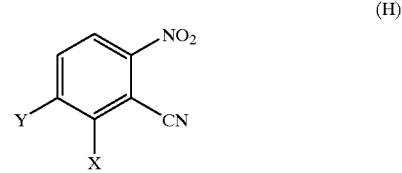

(c) reacting compound (I) under reducing conditions to form a compound of the formula (J):

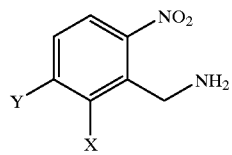
(J)

(d) reacting compound (J) under reducing conditions to form a compound of the formula (K):

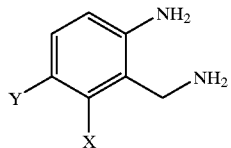
(K)

(e) reacting compound (K) with CNZ to form the desired compound (E) as an HZ salt.

5. The method of claim 4 wherein X and Y are both Cl and Z is Br.

6. A method for making a compound of the formula:

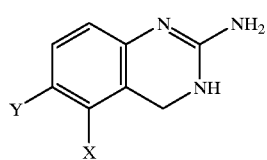
(E)

comprising the steps of:

(a) nitrating a compound of the formula (L):

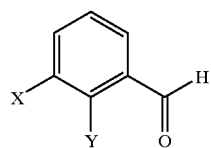
(L)

to form a compound of the formula (M):

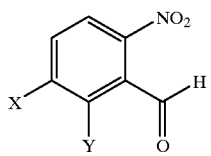
(M)

wherein X and Y are independently Cl, Br or F;

(b) hydroxylating and halogenating compound (M) preferably in situ sequential reactions to form a compound of the formula (O) with intermediate (N):

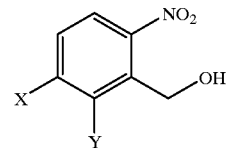
(N)

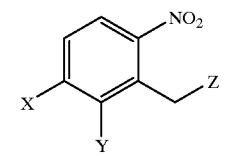
(O)

wherein Z is Cl, Br or F;

(c) aminating compound (O) to form a compound of the formula (P):

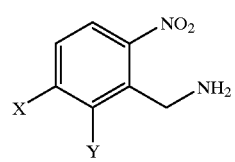
(P)

(d) reducing compound (P) to form a compound of the formula (Q):

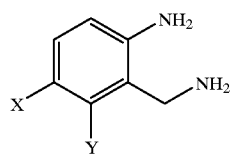
(Q)

(e) cyanating compound (Q) to form the desired compound (E):

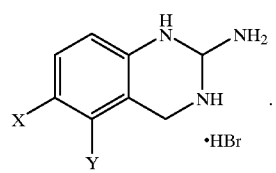
(E)

7. The method of claim 6 wherein X and Y are both Cl.

8. The method of claim 6 wherein compound (M) is reacted to form compound (P) and the process continued to form compound (E).

9. The method of claim 8 wherein both X and Y are Cl.

10. A method of reducing platelet count in a patient which comprises administering to said patient a platelet reducing effective amount of a compound of claim 1 and a pharmaceutically acceptable carrier.

11. The method of claim 10 wherein both X and Y of the compound are Cl.

12. The method of claim 11 wherein the compound is in the form of a HBr salt.

13. A pharmaceutical composition containing as the active ingredient at least one compound as claimed in claim 1 together with pharmaceutically acceptable excipients.

14. The pharmaceutical composition of claim 13 wherein the X and Y of the compound are Cl.

15. The pharmaceutical composition of claim 14 wherein the compound is in the form of a HBr salt.

* * * * *